United States Patent [19]

Chiesi et al.

[11] Patent Number: 4,956,384
[45] Date of Patent: Sep. 11, 1990

[54] 1,4:3,6-DIANHYDROSORBITOL 2-MONONITRATE AND 5-MONONITRATE ESTERS AND PHARMACEUTICAL COMPOSITIONS THEREFROM

[75] Inventors: Paolo Chiesi; Vittorino Servadio, both of Parma, Italy

[73] Assignee: Chiesi Farmaceutici S.p.A., Parma, Italy

[21] Appl. No.: 189,982

[22] Filed: May 4, 1988

[30] Foreign Application Priority Data

May 8, 1987 [IT] Italy ............................... 20438 A/87

[51] Int. Cl.$^5$ ..................... A61K 31/34; C07D 493/04
[52] U.S. Cl. ..................................... 514/470; 549/464

[58] Field of Search .......................... 549/464; 514/470

[56]  References Cited
U.S. PATENT DOCUMENTS 3,886,186  5/1975  Dvonch et al. ..................... 549/464

Primary Examiner—Nicky Chan
Attorney, Agent, or Firm—Bucknam and Archer

[57]  ABSTRACT

Isosorbide 2- and 5-mononitrate esters with aliphatic, aryl, or cynnamic acids or diacids, or with alkylcarbonyloxy substituents optionally containing an isosorbide 2- or 5-mononitrate group, are useful in human therapy.

12 Claims, No Drawings

1,4:3,6-DIANHYDROSORBITOL 2-MONONITRATE AND 5-MONONITRATE ESTERS AND PHARMACEUTICAL COMPOSITIONS THEREFROM

The present invention relates to novel 1,4:3,6-dianhydrosorbitol 2-mononitrate and 5-mononitrate esters, which are respectively also defined isosorbide 2-and 5-mononitrate, to a process for the preparation thereof and to the therapeutic use thereof.

The compounds of the present invention have the following general formulae:

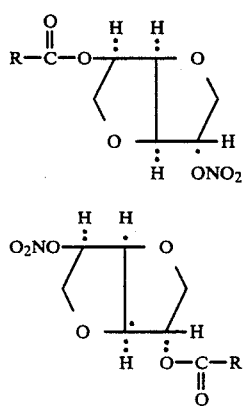

wherein R is:

a straight or branched $C_6$-$C_{18}$ alkyl;

a $C_2$-$C_5$ carboxyalkyl;

a ($C_1$-$C_4$)-alkoxycarbonyl ($C_1$-$C_5$)-alkyl;

a 1,4:3,6-dianhydrosorbitol 2- (or 5-)-nitrate-2 (or 5-)-oxycarbonylethyl group;

a phenylethenyl group, which may be optionally substituted on the aromatic ring by one or more alkoxy groups, preferably methoxy, at any position;

a phenyl group substituted by one or more $C_1$-$C_6$ alkoxy groups.

Particularly representative examples of the invention are compounds wherein R has one of the following meanings:

pentadecyl; 2-carboxyethyl; 4-ethoxycarbonylbutyl; 1,4:3,6 -dianhydrosorbitol 2(or 5)nitrate-2(or 5)oxy-carbonylethyl; (3,4-dimethoxyphenyl)ethenyl; (3,4,5-trimethoxyphenyl)ethenyl; phenylethenyl; 3,4,5-trimethoxyphenyl.

Compounds 1,4:3,6-dianhydrosorbitol 5-nitrate or isosorbide 5-nitrate (IS-5N) and 1,4:3,6-dianhydrosorbitol 2-nitrate or isosorbide 2-nitrate (IS-2N) have been known for a long time and are pharmacologically well-characterized as coronary vasodilators.

Structural characteristics thereof were studied and defined by Hayward et al, Can. J. Chem. 45, 2191(1967) and by Anteunis et al, Org. Magnetic Resonance 3, 693 (1971).

Isosorbide 5-nitrate, particularly, as well as other organic nitrates, is widely used in the therapy of angina attacks, myocardial ischemia and cardiac insufficiency conditions.

Nitro-compounds seem to act through the same mechanism of hemodynamic action, which is rather complex and still not completely clarified by some aspects.

According to one of the more accredited interpretations, nitro-derivatives action is due to intracellular release of $-NO_2$ and therefore of nitrous oxide (NO), which reacts with compounds containing SH groups to form S-nitrosothiols, which are believed to activate guanylcyclase, which on its turn increases cyclic GMP levels causing vasodilation to occur (Ignarro L. e coll. J. Pharmacol. Exp. Ther. 218, 739, 1981). The entire process takes place inside the cell, the basic step consisting therefore the entry of organic nitrates into the cell.

On this ground, it is assumed that the higher nitroderivative liposolubility, the greater activity thereof, larger amounts of nitroderivatives penetrating into the cell, which may be consequently denitrated to nitrous oxide (Noack E. Meth. Find. Exptl. Clin. Pharmacol. 6 (10), 583, 1984).

Such an hypothesis seems to be confirmed for some aliphatic nitro-derivatives (glycerol mono-, di- and trinitrate), in which a direct relationship between liposolubility and activity was ascertained.

Nevertheless, it should be pointed out that structure-activity relationships in these molecules turn out to be extremely simplified, said molecules being straight structures in which lipophilia increase is directly related to the increase in NO groups which may be made available inside the cell.

Cyclic nitro-derivative behaviour is more complex, since also stereochemical factors are involved, which determine nitro-group position. In fact, this group may be in hexo or endo position, remarkably affecting biological reactivity of the molecule, since the group in the endo position would be particularly sterically hindered and therefore less available. Besides isosorbide 2-nitrate, 5-acetate, tested by Noack E. in the above ed work other isosorbide mononitrate esters have been previously prepared. Lower alkanoyl esters ($C_1$-$C_6$) and benzoyl esters of IS-2N and IS-5N are disclosed in British patent no. 1,356,374; some of said compounds proved to reduce significantly systemic blood pressure and coronary resistances. However, no one of these derivatives has hitherto shown real advantages in comparison with already used traditional nitrates.

The results obtained with the compounds of the present invention, though confirming that no direct correlations between liposolubility and activity exist and that structure-activity relationships are more complex, have however permitted to find out some particularly interesting structures, since they show a surprising increase in the vasodilating action, which demonstrates their advantageous use in therapy.

Compounds of general formulae Ia and Ib were prepared according to conventional processes for the esterification of an hydroxy group.

1,4:3,6-dianhydrosorbitol 2-nitrate (IS-2N) and 1,4:3,6-dianhydrosorbitol 5-nitrate (IS-N5) were respectively used as starting materials, said compounds as well as the processes for the preparation thereof being already known. Thus, IS-2N or IS-5N are reacted with an equimolar amount or a slight excess of an aliphatic or aromatic acid, or preferably a reactive derivative thereof, such as the ester or the cyclic or acyclic anhydride, or the acyl chloride, in an aprotic solvent, such as methylene chloride, chloroform, tetrahydrofuran or pyridine.

Where acyl chloride or anhydride are used, the reaction is preferably carried out in the presence of a stoichiometric or catalytic amount of a base or an acid-binding agent, such as tertiary aliphatic or aromatic amines, preferably triethylenamine or dimentylaniline, or in the presence of a base which may also act as the solvent, such as pyridine or dimethylaniline. On the contrary, when the reaction is carried out with anhydrides, strong acids, such as p-toluenesulfonic acid or sulfuric acid, can be used as catalysts.

An alternative synthetic route, particularly suited in the reaction with the acyl chloride, consists of adding an alkali hydride, such as sodium or lithium hydride, to the starting material, IS-2N or IS-5N, and subsequently dropping a solution of the selected acyl chloride into the resulting mixture.

The above reactions are generally carried out at a temperature ranging from 0° C. to the solvent's boiling temperature.

The invention will be now illustrated in more detail by means of the following non-limiting examples.

EXAMPLE 1

1,4:3,6-dianhydrosorbitol 2-(3,4,5-trimethoxy)-benzoate 5-nitrate (II).

19.6 g (0,085 mole) of 3,4,5-trimethoxybenzoyl chloride was added portionwise to a solution of 15 g (0.078 mole) of 1,4:3,6-dianhydrosorbitol 5-nitrate in 70 ml of pyridine, with cooling, to keep temperature at about 20° C. When the addition was over, the temperature was raised to 40° C. for 2 hours to complete the reaction. The reaction mixture was evaporated under reduced pressure and the residue was treated with a mixture of methylene chloride (100 ml) and 5% $Na_2CO_3$ (100 ml).

The organic layer was separated and washed first with a 5% HCl solution, then with water till neutral, then dried over anhydrous sodium sulfate and evaporated. The residue (29 g) was purified by silica gel chromatography, using chloroform as the eluent.

After evaporation of the solvent, 18 g of the white non-crystalline compound was obtained.

MF=$C_{16}H_{20}NO_{10}$ (MW=386.344)$\alpha_D$ (C=0.5% in $CHCl_3$)+75°

By a similar process, using 1,4:3,6-dianhydrosorbitol 5-nitrate and the appropriate acyl chloride as the starting materials, the following compounds were obtained:

1,4:3,6-dianhydrosorbitol 5-nitrate 2-palmitate (III):

MF=$C_{22}H_{39}NO_7$ (MW=429.562); MP=62°-64° C.

1,4:3,6-dianhydrosorbitol 2-(3,4-dimethoxy)cinnamate 5-nitrate:

MF=$C_{17}NO_9$ (MW=381.35); MP=130°-133° C.

1,4:3,6-dianhydrosorbitol 2-cinnamate 5-nitrate (V):

MF=$C_{15}H_{13}NO_7$ (MW=319.277); MP=111°-113° C.

1,4:3,6-dianhydrosorbitol 2-(3,4,5-trimethoxy)cinnamate 5-nitrate:

MF=$C_{18}H_{12}NO_{10}$ (MW=411.373); MP=131°-135° C.

EXAMPLE 2

1,4:3,6-dianhydrosorbitol 5-(3,4-dimethoxy)cinnamate 2-nitrate (VII).

7.5 g (0.033 mole) of 3,4-dimethoxycinnamoyl chloride was added to a solution containing 5.7 g (0.03 mole) of 1,4:3,6-dianhydrosorbitol 2-nitrate in 50 ml of pyridine. The mixture was stirred for 4 hours at 40° C., then poured into 500 ml of water. The product was extracted with methylene chloride, and the organic solution was washed several times with 5% HCl, then with 5% $NaHCO_3$ to neutrality. The mixture was dried over anhydrous sodium sulfate and evaporated, then crystallized from ethyl acetate to obtain 9 g of product (yield 80%), having elemental analysis and IR and NMR spectra in agreement.

MF=$C_{17}H_{19}NO_9$ (MW=381.346); MP=151°-152° C.

By a similar process, using 1,4:3,6-dianhydrosorbitol 2-nitrate and the appropriate acyl chloride as the starting materials, following compounds were obtained:

1,4:3,6-dianhydrosorbitol 2-nitrate 5-palmitate (VIII):

MF=$C_{22}NO_7$ (MW=429.562); MP=60°-63° C.

1,4:3,6-dianhydrosorbitol 5-(3,4,5-trimethoxy)cinnamate 2-nitrate (IX):

MF=$C_{18}H_{21}NO_{10}$ (MW=411.373); MP=101°-103° C.

1,4:3,6-dianhydrosorbitol 5-(3,4,5-trimethoxy)-benzoate 2-nitrate (X):

MF=$C_{16}H_{29}NO_0$ (MW=385.335); MP=146°-147° C.

EXAMPLE 3

1,4:3,6-dianhydrosorbitol 5-nitrate 2-(5-ethoxycarbonyl)pentanoate (XI).

3 g (0.125 mole) of sodium hydride was added portionwise to a solution of 20 g (0.104 mole) of 1,4:3,6-dianhydrosorbitol 5-nitrate in 300 ml of anhydrous tetrahydrofuran. The resulting sodium salt was cooled in an ice bath and reacted with 20.1 g (0.104 mole) of 5-ethoxypentanoyl chloride in anhydrous tetrahydrofuran, carrying out the addition at such a rate to keep temperature below 3° C. The mixture was left under stirring for 1 hour at room temperature, then poured into water. The product was extracted with methylene chloride, washed with water, dried over anhydrous sodium sulfate and evaporated under reduced pressure.

The yellow oily residue was purified by silica gel chromatography, using methylene chloride as the eluent.

15 g of compound (yield: 42%) were obtained.

MF=$C_{14}H_{21}NO_9$ (MW=347.00). $\alpha_D$ (C=0.5% in $CHCl_3$) +108°.

By a process similar to the one described in example 3, using the appropriate starting materials, the following compounds were obtained:

bis-(1,4:3,6-dianhydrosorbitol 5-nitrate-2-il)succinate (XII);

MF=$C_{16}H_{20}N_2O_{14}$ (MW=464.352); MP=124°-132° C.

1,4:3,6-dianhydrosorbitol 2-nitrate 5-(5-ethoxycarbonyl)-pentanoate (XIII);

MF=$C_{14}H_{21}NO_9$ (MW=347.00); $\alpha_D$ (C=0.5% in $CHCl_3$) +85°.

EXAMPLE 4

1,4:3,6-dianhydrosorbitol 5-nitrate 2-(3-carboxy)propionate(XIV).

13 g (0.13 mole) of succinic anhydride was added portionwise to a solution of 20 g (0.11 mole) of 1,4:3,6-dianhydrosorbitol 5-nitrate in 200 ml of pyridine and the mixture was heated to 50° C. for 10 hours. Pyridine was evaporated off under vacuum and the residue was taken up into a 5% sodium carbonate solution. The alkali solution was washed with methylene chloride, acidified with hydrochloric acid and extracted with methylene chloride, dried and evaporated under reduced pressure. Upon crystallization from 800 ml of diisopropyl ether, 15 g of compound was obtained (yield : 50%), having elemental analysis, IR and NMR spectra in agreement.

MF=$C_{10}H_{13}NO_9$ (MW=291.21); MP=64°-67° C.

The activity of the compounds of the present invention was evaluated by means of a number of pharmacological tests in comparison with both the starting mononitrates IS-2N and IS-5N and some alkyl esters of already described nitrates: isosorbide 2-acetate 5-nitrate (IS-2A-5N); isosorbide 5-acetate 2-nitrate (IS-5A-2N); isosorbide 2-nitrate 5-propionate (IS-5P-2N); isosorbide 5-nitrate 2-propionate (IS-2P-5N).

"In vitro" vasodilating activity

Aorta strips from male albino rabbits (New Zealand strain), prepared according to the method by Furchgott and Bhadrakom—J. Pharm. Exp. Ther. 108, 129 (1953), were contracted with a solution enriched in K+ (100 mM). When the contraction was stable, the test compounds were added, according to the method of cumulative dosages.

The responses were isometrically recorded and expressed as contraction percentage inhibition. The concentration causing 50% inhibition ($ED_{50}$) was calculated on the basis of the equation of the linear tract of the dose-response curves. The obtained results expressed as $ED_{50}$ values are reported in tables I and II (which respectively relate to the compounds substituted at the 2-and and 5-positions), together with the values of the octanol/water partition coefficient. The potency ratio for each compound, in comparison with the starting mononitrate, IS-2-N and IS-5-N, is reported in the same tables.

TABLE I

Vasodilating activity of the 2-acyl derivatives of isosorbide 5-nitrate, expressed as $ED_{50}$ (concentration causing a 50% inhibition of contraction of helicoidal strips of rabbit aorta, said contraction being induced by a solution enriched in K+ (100 mM)). Comparison with isosorbide 5-nitrate and respective potency ratios.

| COMPOUND | SUBSTITUENT at the 2-position | Partition coeff. (octanol/$H_2O$) | $ED_{50}$ (M) | Potency ratios (confidence limits) |
|---|---|---|---|---|
| IS-5-N | —OH | 0.891 | $2.53 \times 10^{-4}$ | 1.0 |
| IS-2A-5N | —O—C(=O)—$CH_3$ | 3.79 | $3.39 \times 10^{-5}$ | 8.21 (5.11–13.13) |
| IS-2P-5N | —O—C(=O)—$CH_2$—$CH_3$ | 14.00 | $5.68 \times 10^{-5}$ | 5.19 (3.53–7.52) |
| V | —O—C(=O)—CH=CH—$C_6H_5$ | very high[a] | ND[b] | (≃ 1) |
| XIV | —O—C(=O)—$CH_2$—$CH_2$—COOH | 1.97 | $2.10 \times 10^{-3}$ | 0.16 (0.10–0.25) |
| III | —O—C(=O)—$(CH_2)_{14}$—$CH_3$ | 22.52 | inactive till $10^{-5}$M | |
| II | —O—C(=O)—(3,4,5-trimethoxyphenyl) | 122.70 | $2.72 \times 10^{-6}$ | 113.48 (72.30–172.85) |
| XII | —O—C(=O)—$(CH_2)_2$—C(=O)—O—IS-5-MN | 63.91 | ND[b] | (≃ 20) |
| XI | —O—C(=O)—$(CH_2)_4$—C(=O)—O—$C_2H_5$ | 30.01 | $4.64 \times 10^{-5}$ | 6.91 (4.78–9.88) |

TABLE I-continued

Vasodilating activity of the 2-acyl derivatives of isosorbide 5-nitrate, expressed as $ED_{50}$ (concentration causing a 50% inhibition of contraction of helicoidal strips of rabbit aorta, said contraction being induced by a solution enriched in $K^+$ (100 mM)). Comparison with isosorbide 5-nitrate and respective potency ratios.

| COMPOUND | SUBSTITUENT at the 2-position | Partition coeff. (octanol/$H_2O$) | $ED_{50}$ (M) | Potency ratios (confidence limits) |
|---|---|---|---|---|
| IV | $-O-C(=O)-CH=CH-$ (3,4-di-$OCH_3$ phenyl) | 912.028 | $ND^{(b)}$ | ($\simeq$ 3) |
| VI | $-O-C(=O)-CH=CH-$ (2,4,5-tri-$OCH_3$ phenyl) | 275.100 | $2.74 \times 10^{-5}$ | 7.08 (4.21–11.67) |

ND = not determined.
$^{(a)}$compound remaining exclusively in the octanol phase
$^{(b)}ED_{50}$ was not determined, since at the higher administrable dosage an inhibition lower than 50% was reached.

TABLE II

Vasodilating activity of the 5-acyl derivatives of isosorbide 2-nitrate, expressed as $ED_{50}$ (concentration causing a 50% inhibition of contraction of helicoidal strips of rabbit aorta, said contraction being induced by a solution enriched in $K^+$ (100 mM)). Compression with isosorbide 2-nitrate and respective potency ratios.

| COMPOUND | SUBSTITUENT at the 5-position | Partition coeff. (octanol/$H_2O$) | $ED_{50}$ (M) | Potency ratios (confidence limits) |
|---|---|---|---|---|
| IS-2-N | $-OH$ | 0.588 | $2.39 \times 10^{-5}$ | 1.0 |
| IS-5A-2N | $-O-C(=O)-CH_3$ | 2.62 | $3.97 \times 10^{-6}$ | 6.55 (4.60–9.17) |
| IS-5P-2N | $-O-C(=O)-CH_2-CH_3$ | 8.86 | $1.54 \times 10^{-6}$ | 15.59 (10.74–22.44) |
| VIII | $-O-C(=O)-(CH_2)_{14}-CH_3$ | 32.32 | $ND^{(a)}$ | |
| XIII | $-O-C(=O)-(CH_2)_4-C(=O)-OC_2H_5$ | 38.22 | $3.76 \times 10^{-6}$ | 6.65 (4.81–9.10) |
| VII | $-O-C(=O)-CH=CH-$ (3,4-di-$OCH_3$ phenyl) | 160.018 | $ND^{(a)}$ | ($\simeq$ 1) |
| X | $-O-C(=O)-$ (2,4,5-tri-$OCH_3$ phenyl) | 119.435 | $1.38 \times 10^{-5}$ | 1.58 (1.13–2.19) |

TABLE II-continued

Vasodilating activity of the 5-acyl derivatives of isosorbide 2-nitrate, expressed as $ED_{50}$ (concentration causing a 50% inhibition of contraction of helicoidal strips of rabbit aorta, said contraction being induced by a solution enriched in $K^+$ (100 mM)). Compression with isosorbide 2-nitrate and respective potency ratios.

| COMPOUND | SUBSTITUENT at the 5-position | Partition coeff. (octanol/H₂O) | $ED_{50}$ (M) | Potency ratios (confidence limits) |
|---|---|---|---|---|
| IX | —O—C(=O)—CH=CH—C₆H₂(OCH₃)₃ (3,4,5-trimethoxy) | 314.591 | ND[a] | (≈ 3) |

ND = not determined.
[a] compound remaining exclusively in the octanol phase
[b] $ED_{50}$ was not determined, since at the higher administrable dosage an inhibition lower than 50% was reached.

Hypotensive activity

Male albino rats were used (D strain, Charles River) anesthetized with a starting dose of sodium pentobarbital of 60 mg/kg i.p. and thermoregulated at 37° C. Mean arterious pressure was monitored at right carotidis arteria, while the compounds were administered as a bolus into the jugular vein, at constant volumes of 0.3 and 1 ml/kg.

The results, expressed as $ED_{20}$, dose causing a 20% reduction in the mean arterious pressure (graphically calculated) are expressed in table III, relating to compounds substituted at the 2- and 5-positions.

TABLE III

Hypotensive activity of the compounds of the invention, expressed as $ED_{20}$, dose reducing by 20% the mean arterious pressure (graphically calculated).

| Compound | $ED_{20}$ μmoli/Kg. i.v. | Potency In vivo | ratio In vitro |
|---|---|---|---|
| IS-5-N | 150 | 1 | 1 |
| IS-2A-5N | 2.5 | ≈60 | 8 |
| IS-2P-5N | 2.3 | ≈65 | 5 |
| V | 1.9 | ≈79 | 1 |
| XIV | 300 | ≈0.5 | 0.2 |
| III | ND | — | — |
| II | 1.9 | ≈79 | 113 |
| XII | 7 | ≈21 | 7 |
| XI | 7 | ≈21 | 7 |
| IV | 1.8 | ≈83 | 3 |
| VI | 1.6 | ≈94 | 7 |
| IS-2-N | 12 | ≈1 | 1 |
| IS-5A-2N | 2.2 | ≈5.4 | 6.5 |
| IS-5P-2N | ND | — | 15.6 |
| VIII | ND | — | — |
| XIII | 2.5 | ≈4.8 | 6.6 |
| VII | 0.3 | ≈40 | 1 |
| X | 0.4 | ≈30 | 1 |
| IX | 0.6 | ≈20 | 6 |

The results reported in tables I-III confirm the starting hypotesis that structure-activity relationships starting hypothes. In cyclic nitroderivatives are of complex nature.

The only parameter of lipophilia (expressed by the octanol/water partition coefficient) did not prove to be able to predict by itself a possible higher or lower vasodilating activity.

In fact, in the "in vitro" tests, high lipophilic compounds exerted only a poor vasodilating activity. In other cases, introduction of the same substituent group, even though remarkably and analogously increasing the lipophilia of the starting mononitrate, displayed completely different pharmacological effects. For example, by comparing the behaviour of compounds II and X, reported in tables I and II, one notes that, while IS-5N derivative (compound II) is about 140 times more lipophilic and also about 110 times more active than the starting compound, corresponding IS-2N derivative (compound X), though being 200 times more lipophilic, is only 1.58 times more active than the corresponding mononitrate.

The "in vivo" tests confirmed that vasodilating activity is not directly related to lipophilia.

In fact, screening carried out in the rat evidenced that almost all of the tested compounds show an higher hypotensive activity than starting mononitrates: however, the activity thereof can not be related to the respective lipophilia (table III).

Particularly, one of the compounds, 1,4:3,6-dianhydrosorbitol 2-(3,4,5-trimethoxy)benzoate 5-nitrate (compound II), showed a remarkable hypotensive activity in both "in vitro" and "in vivo" tests.

The above results are confirmed also in another animal species. In the anesthetized rabbit, in vein administration of compound II of the present invention caused a dose-depending reduction in arterious pressure, with a strength about 10 and 100 times higher than that of IS-2N and IS-5N.

A further object of the present invention thus relates to pharmaceutical compositions containing one of the compounds of formulae Ia or Ib as the active ingredient, as such or in form of a pharmaceutically acceptable salt thereof, in combination with pharmaceutically acceptable excipients, said compositions being used in cardiovascular therapy and particularly as coronary vasodilators.

The compositions will be administered by the oral, sublingual, parenteral or topical routes, respectively in form of capsules, tablets, suspensions or emulsions, vials, creams or gels.

For the preparation of pharmaceutical formulations for oral administration in unitary dosage form, the active ingredient can be admixed with a solid powdered excipient, such as lactose, saccharose, sorbitol, mannitol; potato, cereal or mais starch or amylopectin, and can further contain lubricants such as talc, magnesium or calcium stearate, polyethylene glycol or silica.

Tablets may be variously coated according to well-known methods in pharmaceutical technique. Hard gelatin capsules can contain granulates of the active ingredient together with solid, powdered excipients, such as lactose, saccharose, sorbitol, mannitol, starches (of the above indicated type), cellulose or gelatin derivatives, and can also contain stearic acid or magnesium stearate or talc.

Alternatively, particularly in case the active ingredient is an oil, oral compositions will preferably consist in soft gelatin capsules, in which the active ingredient will be present dissolved in a vegetal or mineral oil, or in hard gelatin capsules, in which the active ingredient is admixed with a gelling agent, such as precipitated silica and fatty substances having a melting point higher than 50-60° C.

The unitary dosage for the above described compositions will vary from 20 to 100 mg of active ingredient.

Another type of pharmaceutical composition consists in suspensions or emulsions in which the active ingredient, present at 20 to 50% concentrations, is formulated in appropriate syrup excipients.

In the injectable formulations for parenteral administration, the excipients can be a sterile pharmaceutically acceptable liquid, such as water or a polyvinylpyrrolidone aqueous solution, or an oil, such as peanut oil, and optionally a stabilizing agent and/or a buffer. The active ingredient can be dissolved in the liquid and filter sterilized before placing into vials, or it can be suitably lyophilized, in which case liquid vials containing injection liquid will be added to the confection to obtain the solution before use.

For the preparation of formulations for topical use, fatty excipients such as vaseline, vaseline oil, lanoline, etc. or self-emulsifying excipients, such as fatty alcohols, polyethylene glycols, fatty acid ethers or esters, or other tensides emulsified in water, in case of unguents, can be used.

In case of the preparation of hydrophilic colloid gels, polymers of different nature, such as carboxyvinylpolymers, sodium carboxymethylcellulose, gelified Methogels in water, ethanol, propylene glycol, glycerol, polyethylene glycols etc. can be used.

Topical formulations will be optionally added with appropriate agents favouring penetration of the active ingredient into cutaneous tissue, such as DMSO, pyrrolidone derivatives and so forth.

The above formulations will contain the active ingredient in concentrations from 1 to 10%.

Another particularly advantageous administration method for compounds of formulae Ia and Ib is provided by transdermal systems, consisting in adhesive matrices which can be applied on cutis, in which systems the active ingredient is incorporated at a suitable concentration and is gradually released through cutis, entering into hematic circle.

We claim:

1. 1,4:3,6-dianhydrosorbitol 2- or 5-mononitrate, of general formulae:

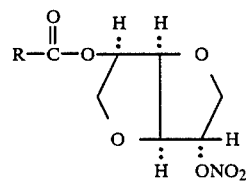

Ia

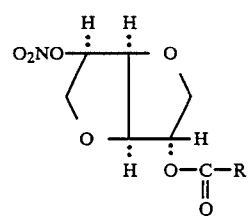

Ib wherein R is:
- a $C_2$–$C_5$ carboxyalkyl
- a ($C_1$–$C_4$)-alkoxycarbonyl ($C_1$–$C_5$)-alkyl;
- a 1,4:3,6-dianhydrosorbitol 2- (or 5)-nitrate-2 (or 5-)oxycarbonylethyl group;
- a phenylethenyl group, which is unsubstituted or substituted on the aromatic ring by one or more lower alkoxy groups, at any positions.

2. A compound as claimed in claim 1, wherein R is 2-carboxyethyl.

3. A compound as claimed in claim 1, wherein R is 4-ethoxycarbonylbutyl.

4. A compound as claimed in claim 1, wherein R is 1,4:3,6-dianhydrosorbitol 2-nitrate 5-oxy-carbonylethyl.

5. A compound as claimed in claim 1, wherein R is 1,4:3,6-dianhydrosorbitol 5-nitrate 2-oxy-carbonylethyl.

6. A compound as claimed in claim 1, wherein R is (3,4-dimethoxyphenyl)ethenyl.

7. A compound as claimed in claim 1, wherein R is (3,4,5-trimethoxyphenyl)ethenyl.

8. A compound as claimed in claim 1, wherein R is phenylethenyl.

9. A pharmaceutical composition containing as the active ingredient 1–15% of one of the compounds as claimed in claim 1 and appropriate pharmaceutically acceptable excipients, for the treatment of angina attacks, myocardial ischemia and cardiac insufficiency conditions.

10. A pharmaceutical composition for oral or sublingual administration, in form of capsules, or tablets, containing 20 to 200 mg of one of the compounds according to claim 1 as the active ingredient in unitary dosage form, or in form of suspensions or emulsions, containing 20 to 50% of said active ingredient.

11. The pharmaceutical composition as claimed in claim 10, for parenteral administration, in form of vials.

12. The pharmaceutical composition as claimed in claim 9, for topical administration, in form of a cream or gel, containing 1 to 10% of said active ingredient, or for transdermal administration.

* * * * *